(12) United States Patent
Estes et al.

(10) Patent No.: US 9,702,819 B1
(45) Date of Patent: Jul. 11, 2017

(54) SURFACE VESSEL WAKE DETECTION

(71) Applicants: Lee E Estes, Mattapoisett, MA (US);
Stephen B Doyle, Wakefield, RI (US)

(72) Inventors: Lee E Estes, Mattapoisett, MA (US);
Stephen B Doyle, Wakefield, RI (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 0 days.

(21) Appl. No.: 15/189,028

(22) Filed: Jun. 22, 2016

(51) Int. Cl.
| | |
|---|---|
| *G01N 21/55* | (2014.01) |
| *G01S 7/481* | (2006.01) |
| *G01S 7/499* | (2006.01) |
| *G01S 17/02* | (2006.01) |
| *G01S 17/88* | (2006.01) |
| *G01N 21/21* | (2006.01) |

(52) U.S. Cl.
CPC ............ *G01N 21/55* (2013.01); *G01N 21/21* (2013.01); *G01S 7/481* (2013.01); *G01S 7/4812* (2013.01); *G01S 7/499* (2013.01); *G01S 17/026* (2013.01); *G01S 17/88* (2013.01); *G01N 2021/216* (2013.01)

(58) Field of Classification Search
CPC ........ G01N 21/21; G01N 21/55; G01N 21/49; G01N 21/53; G01N 2021/551; G01N 2021/4709; G01N 2021/216; G01S 7/4808; G01S 7/481; G01S 7/4811; G01S 7/4812; G01S 7/483; G01S 7/499; G01S 17/00; G01S 17/02; G01S 17/026; G01S 17/06; G01S 17/08; G01S 17/66; G01S 17/88; G01S 17/89; G01S 17/93; G01S 17/933

See application file for complete search history.

(56) References Cited

U.S. PATENT DOCUMENTS

| | | | | |
|---|---|---|---|---|
| 3,005,974 | A * | 10/1961 | Northrup | F42B 19/01 102/418 |
| 4,129,775 | A * | 12/1978 | O'Meara | G01S 7/4811 244/171 |
| 4,862,257 | A * | 8/1989 | Ulich | G01S 17/89 348/144 |
| 4,867,558 | A * | 9/1989 | Leonard | G01K 11/12 356/43 |
| 4,893,924 | A * | 1/1990 | Leonard | G01K 11/12 356/43 |
| 4,963,024 | A * | 10/1990 | Ulich | G01N 21/49 250/574 |

(Continued)

*Primary Examiner* — Gordon J Stock, Jr.
(74) *Attorney, Agent, or Firm* — James M. Kaslschke; Michael P. Stanley

(57) ABSTRACT

A system is provided for detection of surface glints on a water surface. A laser of the system produces a nearly horizontal or vertical linearly polarized laser light pulse. Lens of the system form an afocal imaging system with lateral magnification and longitudinal magnification that projects an image of the laser light at a pulse location onto the water surface. A portion of the laser light is focused onto a high speed detector. The output of the high speed detector is connected to a digitizer to provide system synchronization and to monitor the laser light. A glint image of the pulse location is detected by a broad band detector. The electrical output of the detector is input to the digitizer where the output is digitized. The output of the digitizer is then sent to a computer where the output is stored and analyzed.

5 Claims, 2 Drawing Sheets

(56) References Cited

U.S. PATENT DOCUMENTS

| | | | | |
|---|---|---|---|---|
| 5,013,917 A * | 5/1991 | Ulich | ............... | G01N 21/49 |
| | | | | 250/330 |
| 5,231,401 A * | 7/1993 | Kaman | ............... | G01S 17/89 |
| | | | | 250/332 |
| 5,243,541 A * | 9/1993 | Ulich | ............... | G01S 7/487 |
| | | | | 348/31 |
| 5,550,789 A * | 8/1996 | Silverstien | ............... | G01S 15/523 |
| | | | | 181/0.5 |
| 6,836,285 B1 * | 12/2004 | Lubard | ............... | G01S 7/4802 |
| | | | | 348/31 |
| 7,551,519 B2 * | 6/2009 | Slater | ............... | G01H 9/00 |
| | | | | 367/178 |
| 8,044,999 B2 * | 10/2011 | Mullen | ............... | G01S 7/491 |
| | | | | 348/161 |
| 8,207,484 B1 * | 6/2012 | Williams | ............... | G01C 13/00 |
| | | | | 250/203.6 |
| 8,499,637 B1 * | 8/2013 | Blackmon | ............... | G01N 29/2418 |
| | | | | 367/149 |
| 8,711,344 B1 * | 4/2014 | Estes | ............... | G01N 21/41 |
| | | | | 356/128 |
| 8,953,647 B1 * | 2/2015 | Mead | ............... | H01S 3/06754 |
| | | | | 12/94 |
| 2010/0060901 A1 * | 3/2010 | Martin | ............... | H04B 11/00 |
| | | | | 356/512 |
| 2012/0242533 A1 * | 9/2012 | Shiba | ............... | G01S 7/40 |
| | | | | 342/146 |

* cited by examiner

SURFACE VESSEL WAKE DETECTION

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION (1) Field of the Invention

The present invention is a system and method of use for detection of surface vessels from underwater.

(2) Description of the Prior Art

Surface wakes have been detected using electromagnetic radiation spanning microwave and visible wavelengths. A surface sea state and wake bubble content can provide wake features that are observable under solar illumination. However, underwater detection of the solar illumination is complicated by absorption and light scattering in water. Underwater LIDAR systems operating at blue/green wavelengths have been used to detect wakes by detection of laser pulse back scattered light from wake bubbles.

For microwave frequencies, water absorption is of a magnitude that only above surface detection is possible. Above surface detection of wakes at microwave frequencies use radar that produce signal returns that depend on surface wave height and geometry including an average return from capillary waves over an illuminating microwave beam.

In the art, Lubard et al. (U.S. Pat. No. 6,836,285) discloses a specular return, called "glints", which can vary over orders of magnitude and can be either much larger or much smaller than a volume backscatter return. The difficulty that these different returns cause in estimating the surface position is that the volume back scattered return reaches a peak value only after the laser pulse is entirely within the water volume, while the glint signal reaches a peak when the peak of the pulse arrives at the water surface. The distance between these peaks is based on the laser width.

In Slater (U.S. Pat. No. 7,551,519), a sample block diagram depicts a feed-forward filter element wherein the scintillation corrupted gain reference signal is the DC and subsonic signal components from the photosensitive element. The in-band signal is normalized (divided) by the remote optical receiver link gain estimate derived from the DC carrier and subsonic signal components that significantly reduce unwanted amplitude modulation induced by atmospheric turbulence along a line of sight between a passive long range acoustic sensor and the glint associated with an acousto-optical modulator or associated wake turbulence.

In Lubard et al. (U.S. Pat. No. 7,683,928), two different returns estimate a surface position with a volume backscatter return reaching a peak value only after the laser pulse is entirely within the water volume. The glint surface reaches a peak when the peak of the pulse arrives at the water surface. This data has a relatively coarse resolution.

In Lubard et al. (U.S. Pat. No. 7,688,348), a resultant surface mapping algorithm is applied to existing Streak Tube Imaging Lidar (STIL) data taken during other tests. Working with this data provides insight into the discrimination of volume back scattered from glint.

In Mullen et al. (U.S. Pat. No. 8,044,999), pulsed laser sources are used in underwater laser-imaging systems to temporally discriminate against scattered light and to provide object range information. A typical configuration is broad-beam illumination of the scene and a gated intensified camera receiver—although systems using photomultiplier tube receivers in both single and multiple pixel configurations have also been utilized. The Streak Tube Imaging Lidar (STIL) uses a pulsed laser transmitter in a scanner-less configuration.

Williams (U.S. Pat. No. 8,207,484) discloses that the intensity of the return light received by a sensor channel in a LIDAR system used for detection of submerged objects, varies over a comparatively wide range. It has been estimated that under some conditions, a specular reflection (glint) from the water surface might deliver as many as seven times the photons to a single sensor channel whereas the return signal due to back-scatter could be eight orders of magnitude smaller. Each channel of the streak camera includes a glint detector that receives an output signal of a preamplifier. Each channel asserts an output in a high state in response to detection of an input signal of sufficient magnitude to be associated with a specular reflection from the water surface.

In Mead et al. (U.S. Pat. No. 8,953,647), a block diagram depicts a visible-light sensing/imaging system using a frequency-quadrupled IR laser transmitter system. The system outputs a pulsed waveform (amplitude modulated) transmitted laser beam that detects light in the same narrowband wavelength range and processes the received reflections (which are water-object-interaction to water-detector light signals) to generate two-dimensional and/or three-dimensional image information which is output.

In Shiba (United States Patent Application No. 2012/0242533), an object detection support device is disclosed which supports the detection of an object by deflected waves generated from a transmitter. The transmitter is one part of a device that detects and tracks the object, such as a sonar system, radar system or a LIDAR system used to search, detect or range the object in the water.

Based on the success of existing underwater LIDAR systems, there would be a substantive advantage to make use of strong surface glints observed by an innovative system that can focus and manage an output light pulse onto the water surface.

SUMMARY OF THE INVENTION

Accordingly, it is a general purpose and primary object of the present invention to detect and characterize wakes made by surface vessels from underwater.

To attain the object described, a system is provided that includes a laser capable of projecting a laser pulse to a comparatively small optical spot or pulse location onto a water surface.

When the surface is normal to the laser beam; a comparatively strong glint is directed back to a detector of the system. The frequency of glint occurrence is measured as pulses are scanned across the surface with the average glint strength depending on the sea state of the water surface.

As bubbles generated by the hull and propeller motion (of a ship under detection) rise to the surface; the bubbles carry surfactants that reduce surface tension; thereby, reducing capillary waves. As the laser beam is scanned across the surface for subsequent pulses; the reduced capillary waves cause a decrease in the average surface curvature at glint points; thereby, causing an increase in the strength of the glints and a decrease in the occurrence of glints.

As the host underwater vehicle moves; the scanned returns generate a two-dimensional image of glints. The geometry and amplitudes of this image can be matched in a computer to that of wake data and models to help determine the size, speed and direction of motion of the vehicle as well as the age of the wake. While existing systems use LIDAR systems to detect back scatter from wake bubbles; the glint device of the inventive system herein can also measure returns from the wake bubbles to assist in characterizing an associated vessel.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein.

DETAILED DESCRIPTION OF THE INVENTION

Figure 1:
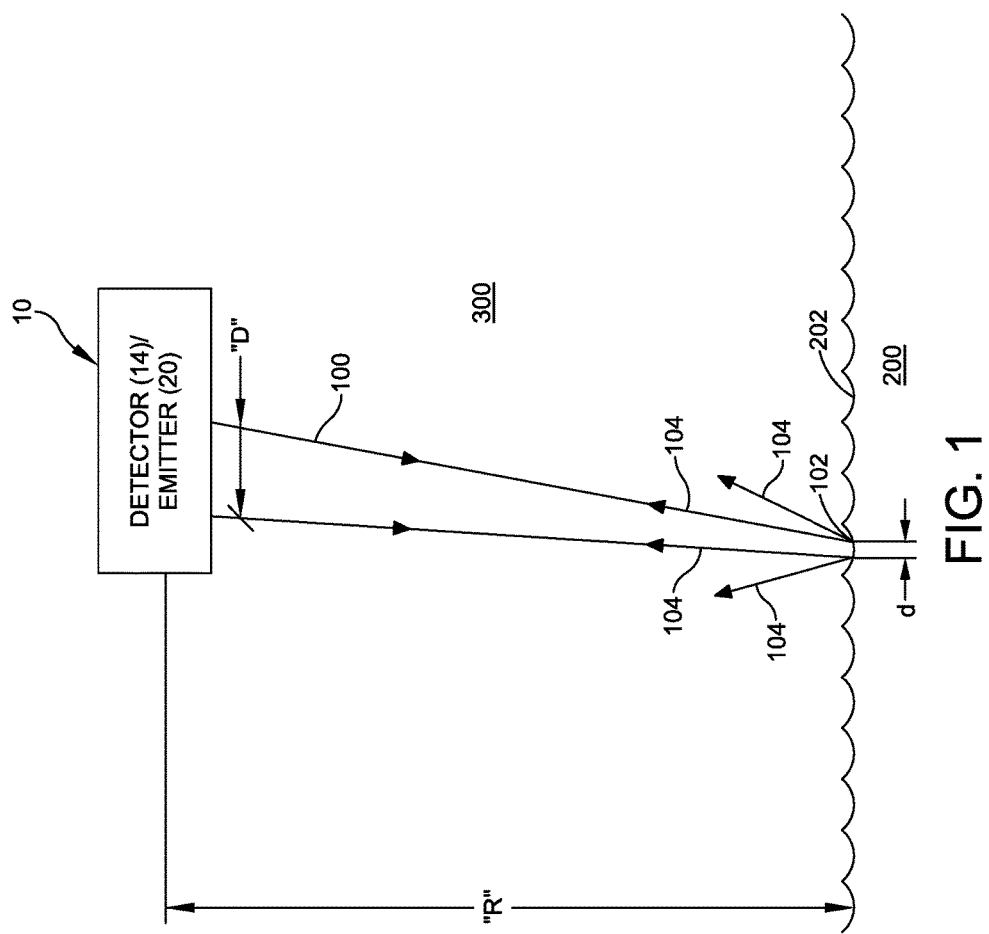
FIG. 1 depicts use of a glint LIDAR system of the present invention.

An underwater glint LIDAR (UGL) system 10 of the present invention is depicted FIG. 1. In the figure, an emitter of the UGL system 10 produces a pulse of laser light beam 100 with a diameter "D". The UGL system 10 focuses the laser light beam 100 onto a pulse location 102 at the water 200, air 300 and water surface 202 at a distance R from the UGL system 10.

If the wavelength of the light in water is $\lambda$ and if the index of refraction variations in the water are neglected; the diameter d, of the focused light at the pulse location 102 is calculated in Equation (1).

$$d = R/D\lambda \quad (1)$$

If the orientation of the water surface 202 is normal to the mean direction of the laser light beam 100 at the pulse location 102; then a glint 104 of laser light is directed back to the UGL system 10. The solid angle, $\Omega$ of the glint 104 is calculated in Equation (2):

$$\Omega = \pi d^2 |C_2|/4 \quad (2)$$

where $C_2$ is the two-dimensional curvature of the water surface 202 at the pulse location 102. Equation (2) assumes that $$|C_2| > \frac{1}{R^2}. \quad (3)$$

Relative to the laser light beam 100, the water surface 202 that generates the glint 104 has a surface height that is a local maximum, minimum, or saddle point at the pulse location 102. If the design of a detector 14 of the UGL system 10 only accepts light that comes from within the focal diameter d, and within the solid angle $$\Omega_r = \frac{\pi D^2}{4R^2}, \quad (4)$$

the portion of the laser light beam 100 that illuminates the detector 14 is $$PD = T_F R_S \frac{\Omega_r}{\Omega} \exp(-2c_\lambda R) = T_F R_S \frac{\lambda^2}{d^4 |C_2|} \exp(-2c_\lambda R) \quad (5)$$

where PD is the symbol for the portion of the laser light, $R_S$ is the surface reflectivity, $T_F$ is the transmission coefficient for the UGL system 10 including an internal interference filter that rejects ambient light outside the spectral bandwidth of the laser light beam 100 and $c_\lambda$ is the coherent attenuation coefficient of the water at a wavelength of the laser light beam 100. The attenuation coefficient, $c_\lambda$, is related to the water absorption, $a_\lambda$, and scatter, $b_\lambda$, coefficients by the closure relationship $$c_\lambda = a_\lambda + b_\lambda \quad (6)$$

Equation (5) neglects laser light that undergoes multiple scattering and appears to be coming from the impact point or pulse location 102 within, d, at the expected time of arrival. Temporal, spatial, and directional filtering (standard matched filtering) within the UGL system 10 discriminates against scattered light.

Interfering light that reaches the detector 14 includes solar light, lunar light, bioluminescence and Cerenkov radiation. If the spectral irradiance (assumed to be Lambertian) falling on an UGL entrance pupil is $I_\lambda$, the light energy $E_D$ that reaches the detector during the light pulse duration, $\tau$, is $$E_D = \frac{\pi}{16} I_\lambda \tau \Delta \lambda T_F \lambda^2 \quad (7)$$

where $\Delta\lambda$ is the spectral width of the UGL interference filter (not shown). Equation (6) shows that the background light of the detector 14 is equal to the light that would illuminate a circular detector with a radius $\lambda/4$. This greatly attenuated background level is due to the temporal, spectral, spatial, and directional filtering incorporated within the UGL system 10.

Figure 2:
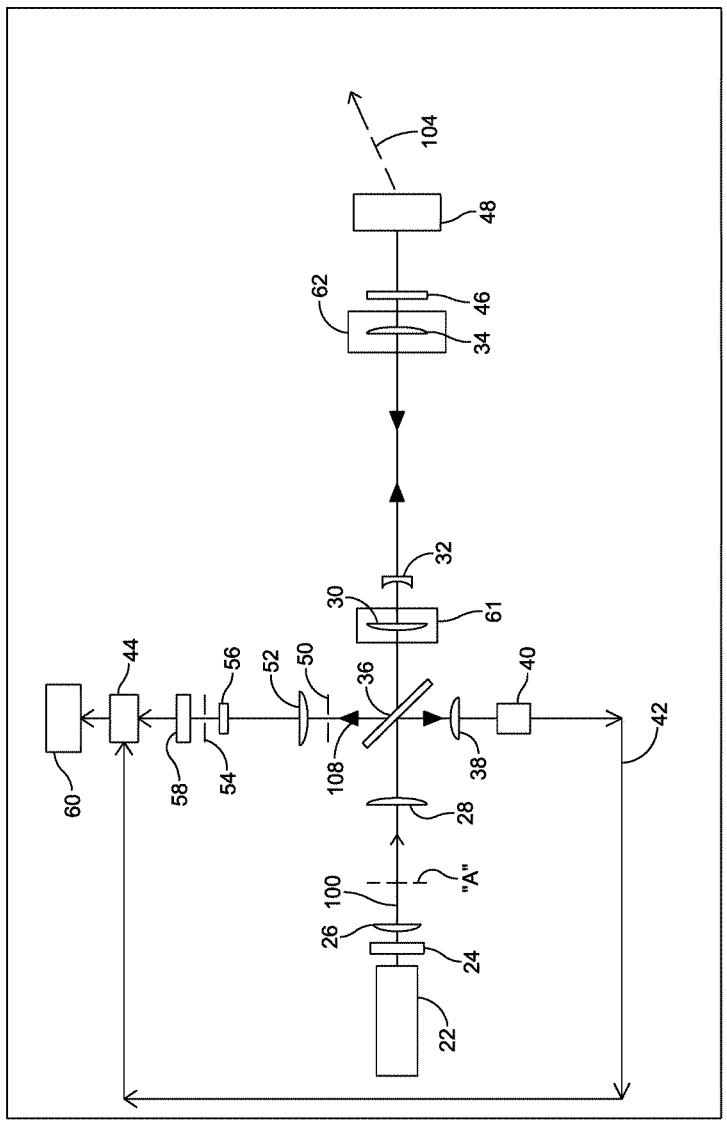
FIG. 2 depicts an implementation of the underwater glint LIDAR of the present invention.

An implementation of the UGL emitter 20 is depicted in FIG. 2. In the figure, a laser 22 generates the pulsed laser light beam 100. Upon exiting the laser 22, the linearly polarized light beam 100 passes thru a half wave plate 24 to create a nearly horizontal or vertical linearly polarized light. A lens 26 focuses the laser light beam 100 to a diameter $d_0$ on a plane "A". Lens 28 and 30 constitute a first unit image magnification telescope that combines with a power telescope comprised of lens 32 and 34 to form an afocal imaging system with lateral magnification M and longitudinal magnification $M^2$ that projects an image of the pulse location 102 at the plane A onto the water surface 202. The diameter, d, of the pulse location 102 is $$d = d_0 |M| \quad (8)$$

The collimated pulse of the laser light beam 100 propagates thru a polarized beam splitter 36 which allows a majority of the laser light beam as linearly polarized light. A small portion of the laser light beam 100, as determined by the angle of the half wave plate 24, is deflected by the polarized beam splitter 36 into a lens 38. The lens 38 focuses the light onto a high speed detector 40.

The output of the high speed detector 40 is connected by a cable 42 to a digitizer 44 to provide system time synchronization and to monitor the laser irradiance light 100. When the output laser light beam 100 passes thru a quarter wave plate 46; the light becomes circularly polarized light. The output laser light beam 100 is directed by an optical scanner 48 to a desired location on the water surface 202.

When the water surface 202 is normal to the light at the point of illumination as the pulse location 102; the glint 104 is reflected back to the UGL system 10. When the glint 104 passes thru a quarter wave plate 48; the light of the glint becomes linearly polarized so that the light can be totally reflected by the polarized beam splitter 36. A reflected glint light beam 108 passes thru a pinhole 50 in which the pinhole has the same diameter as an outgoing collimated beam between the lens 28 and 30. The size of the pinhole 50 assists in rejecting multiple scattered light.

An image of the pulse location 102 is formed by a lens 52 (that has the same focal length as the lens 28). The lens 30 and 52 form a second unit image magnification telescope. The image of the pulse location 102 passes onto a pinhole 54 of a diameter $d_0$. The size of the pinhole 50 assists in rejecting unwanted forward scattered light. The lens 30 and 52 form a telescope so that the optics of the UGL system 10 form a afocal imaging system. An interference filter 56 only passes light at a wavelength of the pulse of laser light beam 100.

The light that passes through the pinhole 54 is detected by a broad band detector 58. The electrical output of the detector 58 is input to the digitizer 44 where the output is digitized. The output of the digitizer 44 is sent to a computer 60 where the output is stored and analyzed. For typical circumstances, the diameter of the pinhole 50 is much larger than $d_0$. The pinhole 50 limits the directional content of the received optical pulse as an aperture of size D at the output of the UGL system 10.

Because the transmitter and receiver optics of the UGL system 10 are afocal; the same spot size can be focused at a different R by translating the lens 30 and lens 34 telescope. This can be accomplished by mounting lens 30 and 34 on motorized translation stages 61 and 62 that are controlled by the computer 60. The scan angle range and rate can also be controlled by the computer 60.

When the UGL system 10 is mounted to a moving underwater vehicle, the system can form an image of glint signal occurrence, location, and strength. The computer 60 can compare the glint image to wake models and recorded data for various surface ships to help determine the characteristics of the surface vessel including the age of the wake created; vessel size and the distance to the vessel.

Recording the time and strength of all light returns will include the returns generated by back scattering from wake bubbles. While the bubble returns are much weaker that the glint returns; the bubble data can also be analyzed to improve the quality of the surface vessel characteristic measurements.

While the primary of the UGL system 10 is from underwater; the system can also be operated from above the water surface 202.

A new feature and major advantage of the UGL system 10 is the use of strong strength glints as compared with bubble LIDAR systems. The glint characteristics also serve as a general measure of sea state and a sensor of unwanted surface pollutants such as oil slicks. If the UGL system 10 is implemented with the afocal optics of FIG. 2; the system can be operated in water of different clarity or at a different stand-off distance by a simple translation of the output telescope to adjust the output focal range. The temporal, spatial, spectral, and directional filtering employed in the UGL system discriminates greatly against background light making operation in daylight and high background environments realistic. The incorporation of the UGL output scanner provides spatial detail in the scan direction.

Alternatives can include any optical implementation that possesses the characteristics ascribed to the UGL system 10 of FIG. 1. can be used to implement the glint detection. If a given application dictates above surface operation; the glint detection can be operated from above the surface.

The foregoing description of the preferred embodiments of the invention has been presented for purposes of illustration and description only. It is not intended to be exhaustive nor to limit the invention to the precise form disclosed; and obviously many modifications and variations are possible in light of the above teaching. Such modifications and variations that may be apparent to a person skilled in the art are intended to be included within the scope of this invention as defined by the accompanying claims.

What is claimed is:
1. A system for detection of glints on a water surface, said system comprising:
   a laser capable of emitting at least one pulse of a laser light beam of a diameter D onto a pulse location at the water surface;
   a half wave plate operationally connected to said laser wherein said half wave plate is capable of creating linearly polarized light of the at least one pulse of laser light beam;
   a first lens operationally connected to said half wave plate opposite to a side of said half wave plate connected to said laser wherein said first lens is capable of focusing the at least one pulse of a light beam to a diameter $d_0$;
   a first unit image magnification telescope including a first magnification telescope lens and a second magnification telescope lens, said first magnification telescope lens operationally connected to said first lens opposite to a side of said first lens connected to said half wave plate;
   a power telescope including a first power telescope lens and a second power telescope lens, said first power telescope lens operationally connected to said second magnification telescope lens on an opposite side of said second magnification telescope lens connected to first magnification telescope lens;
   a polarizing beam splitter positioned between said second magnification telescope lens of said first unit image magnification telescope and said first magnification telescope lens wherein said polarizing beam splitter is capable of deflecting a portion of the at least one pulse of a laser light beam;
   a second lens operationally connected to said polarizing beam splitter wherein said second lens is capable of focusing the portion of the at least one pulse of a laser light beam from said polarizing beam splitter;
   a high speed detector operationally connected to said second lens opposite to a side of said second lens connected to said polarizing beam splitter, wherein said high speed detector is capable of receiving the portion of the at least one light pulse of a laser light beam;
   a digitizer operationally connected to said high speed detector via a cable opposite to a side of said high speed detector connected to said second lens wherein said digitizer is capable of monitoring the portion of the at least one light pulse;
   a quarter wave plate operationally connected to said second telescope lens of said power telescope wherein said quarter wave plate is capable of emitting the at least one light pulse as circularly polarized light;

a second unit image magnification telescope including said second telescope lens of said first magnification telescope as a first telescope lens of said second magnification telescope and including a second magnification telescope lens of said second unit image magnification telescope, said second magnification telescope lens of said second unit image magnification telescope operationally connected to said polarizing beam splitter separate from a connection of said polarizing beam splitter to said second lens;

a first section positioned between said polarizing beam splitter and said second magnification telescope lens of said second unit image magnification telescope, said first section including an aperture sized to the diameter of the at least one light pulse;

an interference filter operationally connected to said second magnification telescope lens of said second unit image magnification telescope on a side of said second magnification telescope lens of said second unit image magnification telescope connected to said first section, said interference filter capable of passing light only at a wavelength of the at least one pulse of a laser light beam;

a second section operationally connected to said interference filter opposite to a side of said interference filter connected to said second magnification telescope lens of said second unit image magnification telescope, said second section including an aperture sized to the diameter of the at least one pulse;

a broad band detector operationally connected to said second section on a first side opposite to a side of said second section operationally connected to said interference filter and said broad band detector operationally connected to said digitizer opposite said first side; and a computer operationally connected to said digitizer opposite to a side connected to said broad band detector;

wherein a combination of said first telescope lens of said second unit magnification telescope and second telescope lens of said second unit magnification telescope is capable of afocal imaging with a lateral magnification M and a longitudinal magnification $M^2$ that projects an image of the pulse location;

wherein the image of the pulse location is reflected as at least one glint from the water surface and can be received by said quarter wave plate to become a linearly polarized light so that the linearly polarized light can be reflected by said polarizing beam splitter;

wherein said digitizer is capable of receiving output of the at least glint from said broadband detector and said computer is capable of receiving output from said digitizer for analyzing the output.

2. A method for detection of glints on a water surface; said method comprising the steps of:

providing an emitter, a detector, a high speed detector, a digitizer and an interference filter;

emitting at least one pulse of a laser light beam onto a pulse location with the emitter at a diameter D to the water surface with the at least one pulse of a laser light beam being circularly polarized light;

sending a portion of the at least one pulse of laser light beam to the high speed detector;

monitoring the portion of the at least one pulse of laser light beam subsequent to said sending step, with the digitizer;

detecting at least one glint on the water surface wherein the step of detecting at least one glint on the water surfaces comprises:

imaging the at least one glint;

filtering the image from said imaging step with the interference filter such that light only passes that is a wavelength of the at least one pulse of laser light beam; and detecting the image with the detector subsequent to said filtering step.

3. The method in accordance with claim 2, said method further comprising the step of determining a diameter $d_0$ of focused light at the pulse location by $d_0 = R/D\lambda$ where R is a distance from the emitter to the water surface and $\lambda$ is the wavelength of the pulsed laser light beam in water.

4. The method in accordance with claim 3, said method further comprising the step of determining a solid angle $\Omega$ of the at least one glint by $\Omega = \pi d^2 |C_2|/4$ where $C_2$ is the two-dimensional curvature of the water surface at the pulse location.

5. The method in accordance with claim 4 wherein a portion PD of the at least one glint that illuminates the detector is $$PD = T_F R_S \frac{\Omega_r}{\Omega} \exp(-2c_\lambda R) = T_F R_S \frac{\lambda^2}{d^4 |C_2|} \exp(-2c_\lambda R)$$

where $R_S$ is the surface reflectivity, $T_F$ is the transmission coefficient and $c_\lambda$ is the coherent attenuation coefficient of the water at a wavelength of the laser light pulse.

* * * * *